(12) United States Patent
Parker (10) Patent No.: US 11,348,438 B1
(45) Date of Patent: May 31, 2022

(54) CARBON MONOXIDE DETECTION SYSTEM

(71) Applicant: William C. Parker, Farmington Hills, MI (US)

(72) Inventor: William C. Parker, Farmington Hills, MI (US)

( * ) Notice: Subject to any disclaimer, the term of this patent is extended or adjusted under 35 U.S.C. 154(b) by 0 days.

(21) Appl. No.: 17/318,574

(22) Filed: May 12, 2021

(51) Int. Cl.
*G08B 21/14* (2006.01)
*G01N 33/00* (2006.01)
*G08B 25/10* (2006.01)

(52) U.S. Cl.
CPC .......... *G08B 21/14* (2013.01); *G01N 33/004* (2013.01); *G08B 25/10* (2013.01)

(58) Field of Classification Search
CPC ....... G08B 21/14; G08B 25/01; G01N 33/004
See application file for complete search history.

(56) References Cited

U.S. PATENT DOCUMENTS

| | | | |
|---|---|---|---|
| D431,487 S | 10/2000 | Rienks | |
| 8,669,878 B1 | 3/2014 | Vantilburg | |
| 8,803,696 B1 | 8/2014 | Dunyan | |
| 9,060,683 B2* | 6/2015 | Tran .................. | H04M 3/42042 |
| 9,811,994 B1 | 11/2017 | Salzer | |
| 9,982,471 B2 | 5/2018 | Ozkan | |
| 10,062,233 B1* | 8/2018 | Rogers ................. | G08B 27/001 |
| 2003/0052792 A1* | 3/2003 | Koyano ................. | G08B 21/14 |
| | | | 340/632 |
| 2004/0032335 A1* | 2/2004 | Parrish ................. | G08B 29/145 |
| | | | 340/628 |
| 2010/0171588 A1* | 7/2010 | Chutorash ............. | E05F 15/668 |
| | | | 340/5.71 |
| 2013/0063259 A1* | 3/2013 | Kramer .................. | G08C 17/02 |
| | | | 340/539.11 |
| 2013/0342342 A1* | 12/2013 | Sabre ...................... | G09F 13/18 |
| | | | 340/509 |
| 2016/0377305 A1* | 12/2016 | Kwa ........................ | F24F 11/30 |
| | | | 700/277 |
| 2018/0151006 A1* | 5/2018 | Huggins ........... | H04M 1/72412 |
| 2018/0266163 A1 | 9/2018 | Combe | |
| 2018/0345859 A1* | 12/2018 | Zehr ...................... | G08B 21/14 |
| 2020/0018469 A1* | 1/2020 | Kohen .................... | F21V 21/02 |
| 2021/0095514 A1* | 4/2021 | Madden ................. | G08B 21/14 |
| 2021/0108818 A1* | 4/2021 | Amundson ............. | H04W 4/12 |
| 2021/0222877 A1* | 7/2021 | Combe .................... | F24F 11/33 |
| 2021/0287509 A1* | 9/2021 | Shepard ................. | G08B 17/10 |

FOREIGN PATENT DOCUMENTS

WO 2018170187 9/2018

* cited by examiner

*Primary Examiner* — Ojiako K Nwugo (57) ABSTRACT

A carbon monoxide detection system for alerting users to dangerous carbon monoxide levels and automatically opening garage doors includes a detection unit comprising a a power source and a CPU coupled within the housing. A carbon monoxide sensor, an alarm, and a control button are coupled to the housing and are in operational communication with the CPU. A transceiver is coupled within the housing and is in operational communication with the CPU. A garage door controller is coupled to the housing and is in operational communication with the CPU as well as with a standard garage door opener. A plurality of voice annunciating units is in wireless communication with the transceiver of the detection unit to create a visual and auditory alert when the alarm is triggered.

10 Claims, 7 Drawing Sheets

CARBON MONOXIDE DETECTION SYSTEM

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to carbon monoxide detection devices and more particularly pertains to a new carbon monoxide detection device for alerting users to dangerous carbon monoxide levels and automatically opening garage doors.

(2) Description of Related Art Including Information Disclosed Under 37 CFR 1.97 and 1.98

The prior art relates to carbon monoxide detection devices. Some existing systems require integration with a vehicle, while others require multiple different components to interact with garage door openers, emergency service auto-dialers, gas lines, and the like. Other existing systems incorporate a specific garage door opener and do not function with generic mechanisms.

BRIEF SUMMARY OF THE INVENTION

An embodiment of the disclosure meets the needs presented above by generally comprising a detection unit comprising a housing having a housing front side, a housing backside, a housing left side, a housing right side, a housing top side, and a housing bottom side. A power source and a CPU are coupled within the housing. The CPU is in operational communication with the power source. A carbon monoxide sensor is coupled to the housing and is in operational communication with the CPU. An alarm is coupled to the housing and is in operational communication with the CPU. A control button is coupled to the housing and is in operational communication with the CPU. A transceiver is coupled within the housing and is in operational communication with the CPU and the voice annunciating units. A garage door controller is coupled to the housing and is in operational communication with the CPU. The garage door controller is configured to be in operational communication with a standard garage door opener. A plurality of voice annunciating units is in wireless communication with the transceiver of the detection unit to create a visual and auditory alert when the alarm is triggered.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
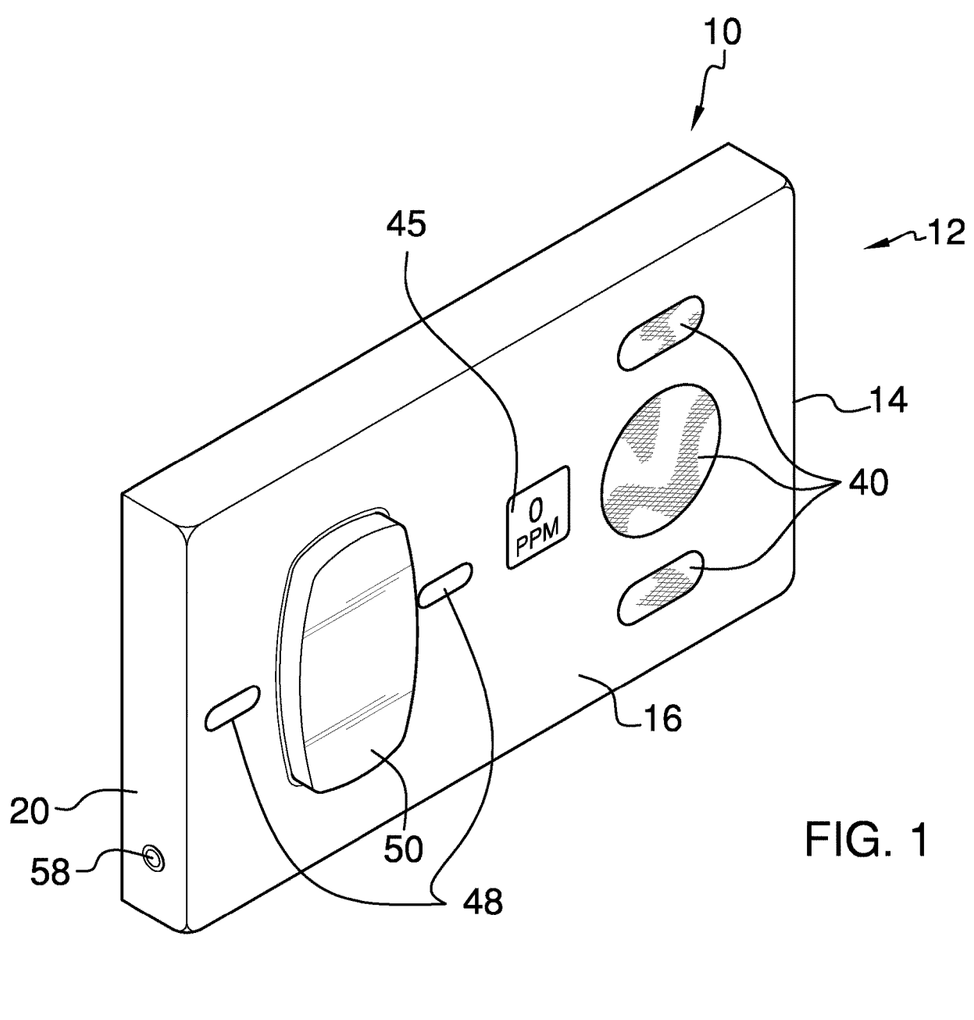
FIG. 1 is an isometric view of a carbon monoxide detection system according to an embodiment of the disclosure.
Figure 2:
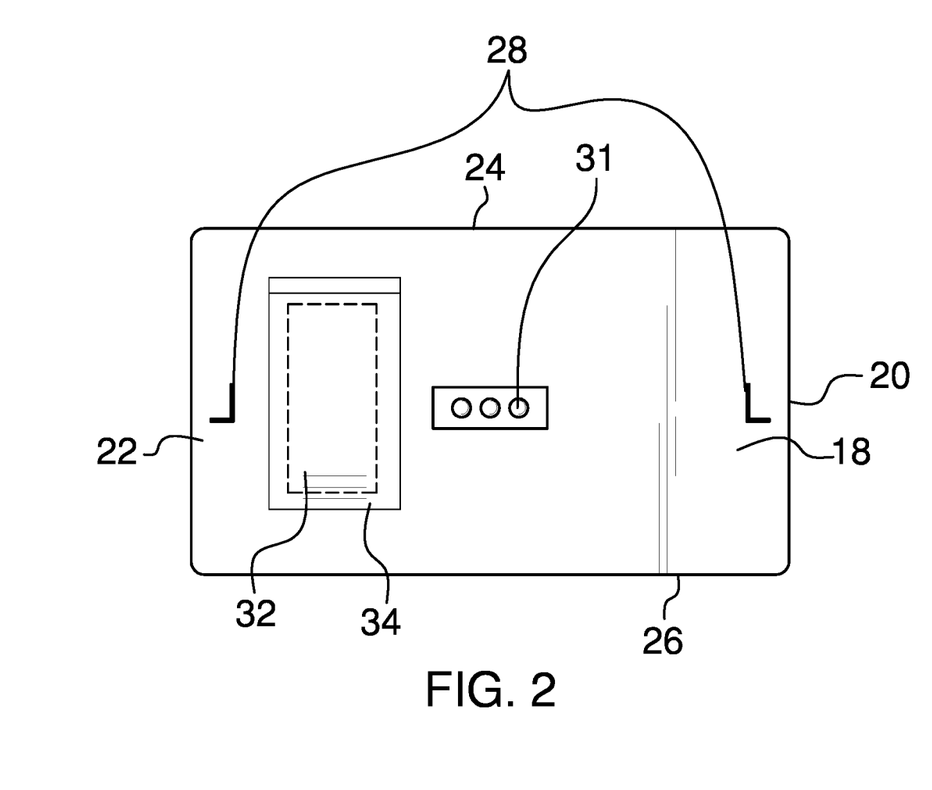
FIG. 2 is a rear elevation view of an embodiment of the disclosure.
Figure 2A:
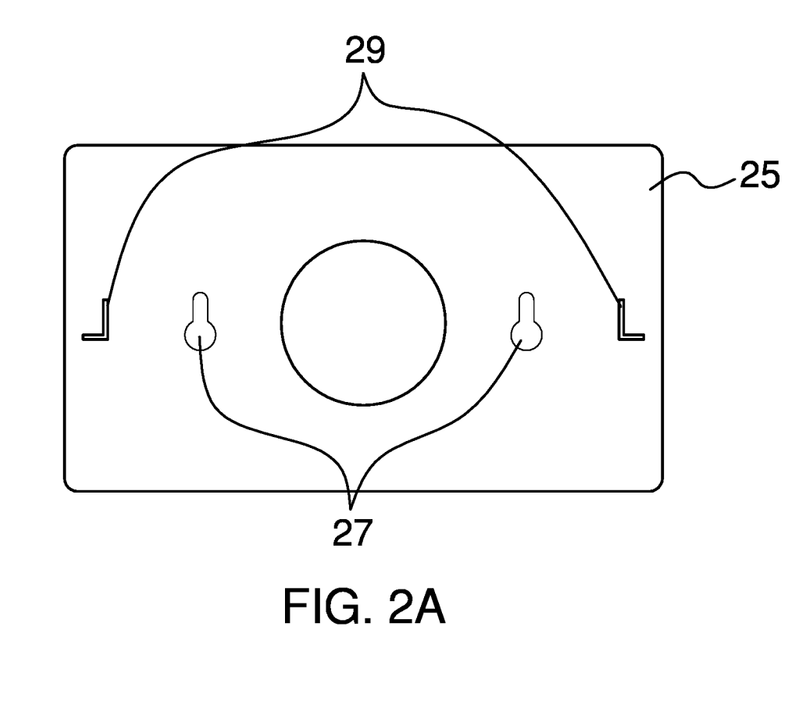
FIG. 2A is a detail view of an embodiment of the disclosure.
Figure 3:
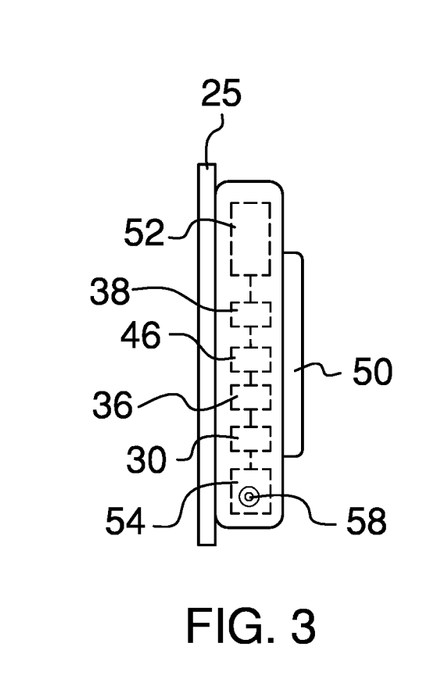
FIG. 3 is a side elevation view of an embodiment of the disclosure.
Figure 4:
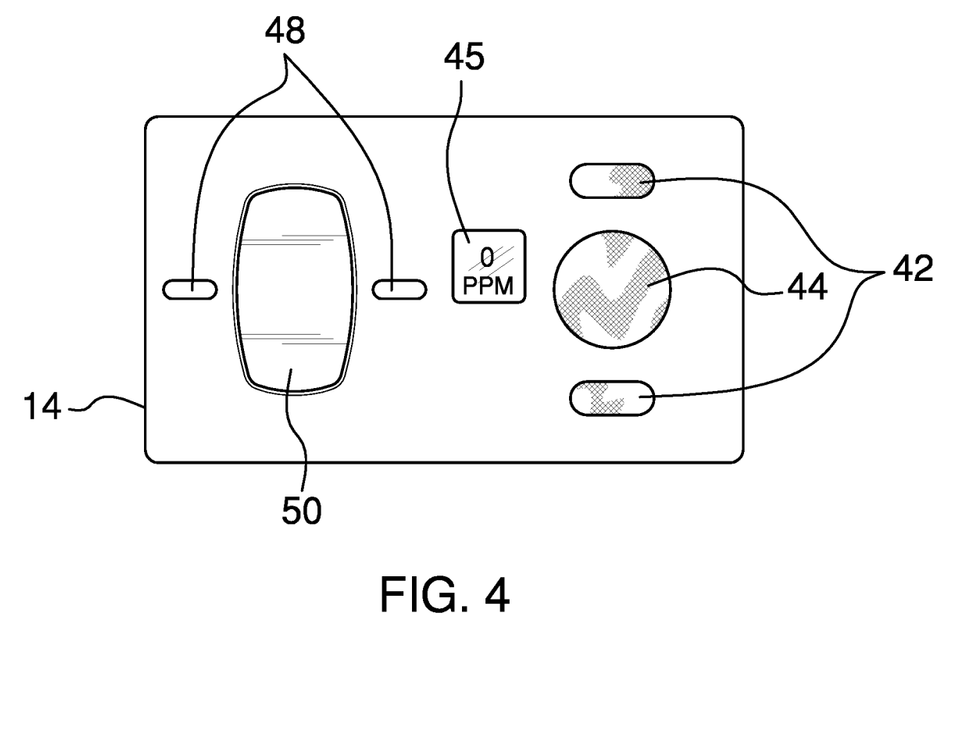
FIG. 4 is a front elevation view of an embodiment of the disclosure.
Figure 5:
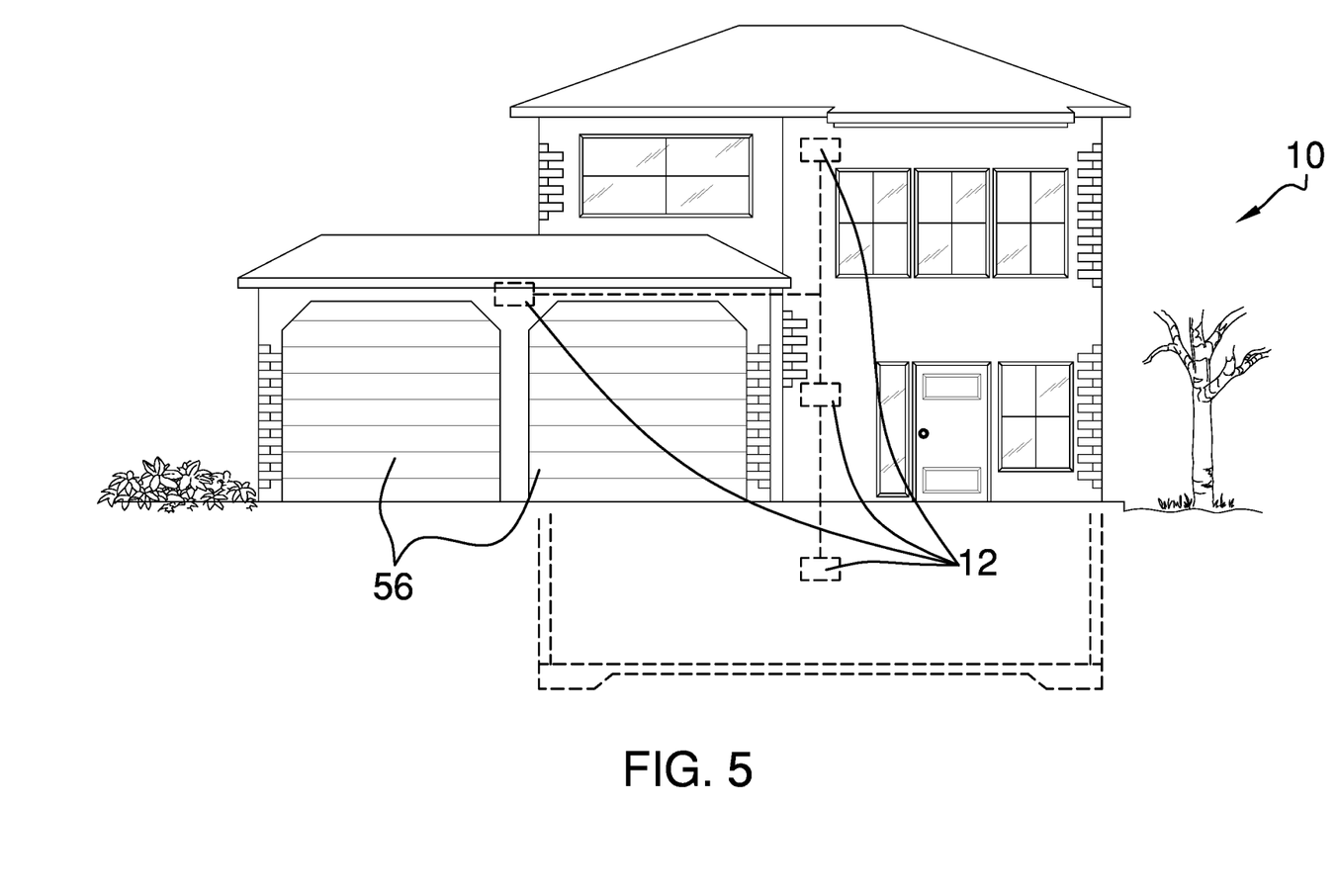
FIG. 5 is an in-use view of an embodiment of the disclosure.
Figure 6:
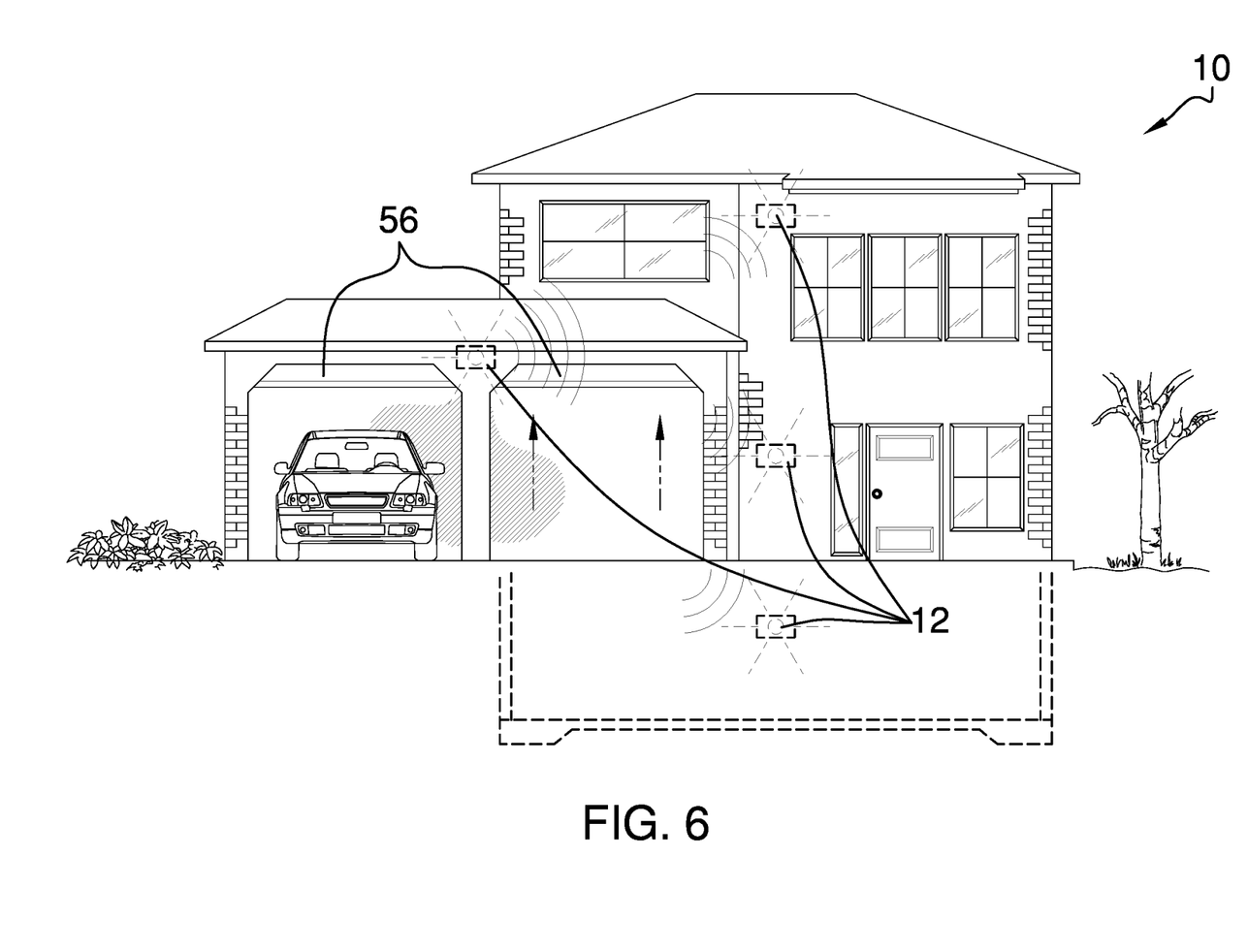
FIG. 6 is an in-use view of an embodiment of the disclosure.
Figure 7:
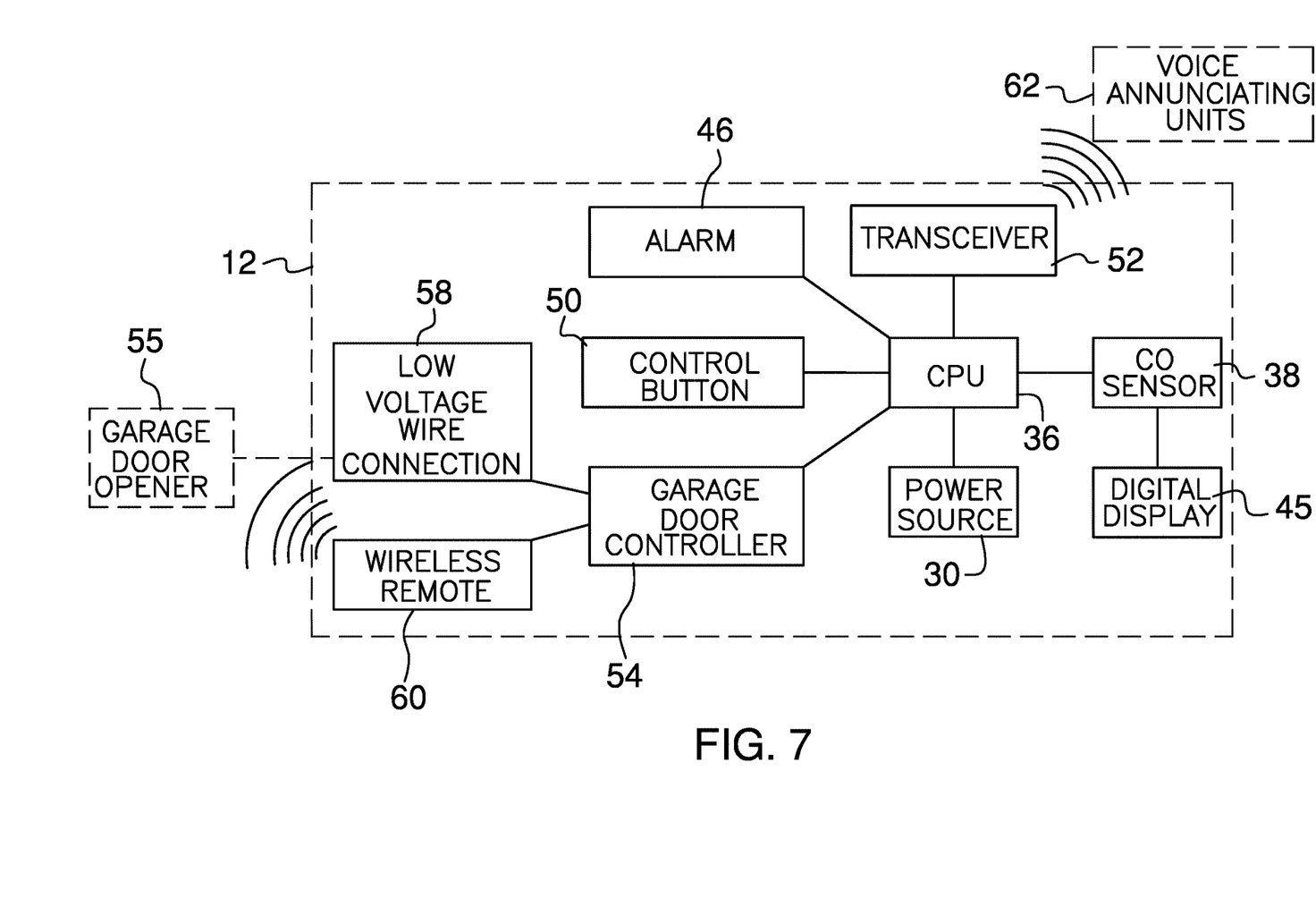
FIG. 7 is a block diagram of an embodiment of the disclosure.

With reference now to the drawings, and in particular to FIGS. 1 through 7 thereof, a new carbon monoxide detection device embodying the principles and concepts of an embodiment of the disclosure and generally designated by the reference numeral 10 will be described.

As best illustrated in FIGS. 1 through 7, the carbon monoxide detection system 10 generally comprises a detection unit 12 comprising a housing 14 having a housing front side 16, a housing backside 18, a housing left side 20, a housing right side 22, a housing top side 24, and a housing bottom side 26. The housing backside 18 may have a pair of engagement slots 28 to selectively couple to a mounting plate 25. The mounting plate 25 has a pair of mounting apertures 27 configured to receive a pair of screws inserted into a wall and a pair of L-shaped engagement hooks 29 to selectively engage the pair of engagement slots 28.

A power source 30 is coupled within the housing 14. The power source 30 may be hardwired to a 120v source with a three pin connector 31 and may include a battery 32 for backup power. The housing back side 18 has a removable battery cover 34 to selectively expose the battery 32 for replacement. A CPU 36 is coupled within the housing 12 and is in operational communication with the power source 30.

A carbon monoxide sensor 38 is coupled to the housing 14 and is in operational communication with the CPU 36. The carbon monoxide sensor 38 may include a plurality of sensor faces 40 extending through the housing front side 16. The plurality of sensor faces 40 may include a pair of obround sensor faces 42 and a medial circular sensor face 44. There may be a digital display 45 coupled to the housing 14 and in operational communication with the carbon monoxide sensor 38 and the CPU 36 to show the level of carbon monoxide detected in the air.

An alarm 46 is coupled to the housing 14 and is in operational communication with the CPU 36. The alarm 46 may include a visual element and an auditory element. The alarm 46 may have a pair of speakers 48 extending through the housing front side 16. The alarm 46 is activated when the carbon monoxide sensor 38 detects unsafe levels of carbon monoxide. A control button 50 is coupled to the housing 14 and is in operational communication with the CPU 36. The control button 50 may be used to silence and reset the alarm 46 and may also be used to test the alarm 46. The control button 50 extends through the housing front side 16 and may be translucent to emit light from the visual element of the alarm 46.

A transceiver 52 is coupled within the housing 14 and is in operational communication with the CPU 36. The transceiver 52 may additionally be configured to be in operational communication with a smartphone and with emergency services.

A garage door controller 54 is coupled to the housing 14 and is in operational communication with the CPU 36. The garage door controller 54 is configured to be in operational communication with a standard garage door opener 55 to open a garage door 56 when the carbon monoxide sensor 38 detects unsafe levels of carbon monoxide. The garage door controller 54 may include a low voltage wire connection 58 configured to receive standard low voltage wiring used for garage door control switches. The garage door controller 54 may also include a wireless remote 60 configured to be in operational communication with the standard garage door opener 55.

A plurality of voice annunciating units 62 is in wireless communication with the transceiver 52 of the detection unit to create a visual and auditory alert when the alarm 46 is triggered.

In use, the detection unit 12 is mounted in the garage with the plurality of voice annunciating units 62 mounted in other areas of a home. When the carbon monoxide sensor 38 of the detection unit 12 detects unsafe levels of carbon monoxide the alarm 46 is activated and the transceiver 52 activates the plurality of voice annunciating units 62. The garage door controller 54 of the detection unit 12 in the garage also automatically opens the garage doors.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A carbon monoxide detection system comprising:
   a detection unit comprising:
      a housing having a housing front side, a housing backside, a housing left side, a housing right side, a housing top side, and a housing bottom side;
      a power source coupled within the housing;
      a CPU coupled within the housing, the CPU being in operational communication with the power source;
      a carbon monoxide sensor coupled to the housing, the carbon monoxide sensor being in operational communication with the CPU, the carbon monoxide sensor including a plurality of sensor faces extending through the housing front side;
      an alarm coupled to the housing, the alarm being in operational communication with the CPU;
      a control button coupled to the housing, the control button being in operational communication with the CPU;
      a transceiver coupled within the housing, the transceiver being in operational communication with the CPU; and
      a garage door controller coupled to the housing, the garage door controller being in operational communication with the CPU and configured to be in operational communication with a standard garage door opener; and
   a plurality of voice annunciating units, each voice annunciating unit being in wireless operational communication with the transceiver of the detection unit to create a visual and auditory alert when the alarm is triggered.

2. The carbon monoxide detection system of claim 1 further comprising the plurality of sensor faces including a pair of obround sensor faces and a medial circular sensor face.

3. The carbon monoxide detection system of claim 1 further comprising the housing backside having a pair of mounting apertures.

4. The carbon monoxide detection system of claim 1 further comprising the control button extending through the housing front side.

5. The carbon monoxide detection system of claim 1 further comprising the control button being translucent; the alarm including a visual element emitting light through the control button.

6. The carbon monoxide detection system of claim 1 further comprising the alarm including an auditory element, the alarm having a pair of speakers extending through the housing front side.

7. The carbon monoxide detection system of claim 1 further comprising the power source including a battery; the housing back side having a removable battery cover to selectively expose the battery.

8. The carbon monoxide detection system of claim 1 further comprising the garage door controller including a low voltage wire connection configured to receive standard low voltage wiring used for garage door control switches.

9. The carbon monoxide detection system of claim 8 further comprising the garage door controller including a wireless remote configured to be in operational communication with the standard garage door opener.

10. A carbon monoxide detection system comprising:
a detection unit, comprising:
- a housing having a housing front side, a housing backside, a housing left side, a housing right side, a housing top side, and a housing bottom side, the housing backside having a pair of mounting apertures;
- a power source coupled within the housing, the power source including a battery; the housing back side having a removable battery cover to selectively expose the battery;
- a CPU coupled within the housing, the CPU being in operational communication with the power source;
- a carbon monoxide sensor coupled to the housing, the carbon monoxide sensor being in operational communication with the CPU, the carbon monoxide sensor including a plurality of sensor faces extending through the housing front side, the plurality of sensor faces including a pair of obround sensor faces and a medial circular sensor face;
- an alarm coupled to the housing, the alarm being in operational communication with the CPU, the alarm including a visual element and an auditory element, the alarm having a pair of speakers extending through the housing front side;
- a control button coupled to the housing, the control button being in operational communication with the CPU, the control button extending through the housing front side, the control button being translucent and emitting light from the visual element of the alarm;
- a transceiver coupled within the housing, the transceiver being in operational communication with the CPU; and
- a garage door controller coupled to the housing, the garage door controller being in operational communication with the CPU and configured to be in operational communication with a standard garage door opener, the garage door controller including a low voltage wire connection configured to receive standard low voltage wiring used for garage door control switches, the garage door controller including a wireless remote configured to be in operational communication with the standard garage door opener; and
- a plurality of voice annunciating units, each voice annunciating unit being in wireless operational communication with the transceiver of the detection unit to create a visual and auditory alert when the alarm is triggered.

* * * * *